United States Patent [19]
Hamlin et al.

[11] Patent Number: 6,129,690
[45] Date of Patent: Oct. 10, 2000

[54] UNIDIRECTIONAL RESISTANCE PIVOT ASSEMBLY FOR A SPLINT

[75] Inventors: Robert N. Hamlin, Bayport; John Thomas VanScoy, St. Paul; Timothy Gearling Haines, Stillwater, all of Minn.

[73] Assignee: EMPI Corp., St. Paul, Minn.

[21] Appl. No.: 09/124,797

[22] Filed: Jul. 29, 1998

[51] Int. Cl.⁷ .................................................. A61F 5/00
[52] U.S. Cl. ............................................................ 602/16
[58] Field of Search ................................. 482/114; 602/5, 602/16, 26

[56] References Cited

U.S. PATENT DOCUMENTS

| | | |
|---|---|---|
| 4,433,679 | 2/1984 | Mauldin et al. . |
| 4,520,804 | 6/1985 | DiGeorge . |
| 5,036,837 | 8/1991 | Mitchell et al. . |
| 5,052,379 | 10/1991 | Airy et al. . |
| 5,203,766 | 4/1993 | Carter et al. . |
| 5,328,446 | 7/1994 | Bunnell et al. ............................ 602/16 |
| 5,399,154 | 3/1995 | Kipnis et al. . |
| 5,407,420 | 4/1995 | Bastyr et al. . |
| 5,437,619 | 8/1995 | Malewicz et al. . |
| 5,520,625 | 5/1996 | Malewicz . |
| 5,520,627 | 5/1996 | Malewicz . |
| 5,571,078 | 11/1996 | Malewicz . |
| 5,749,840 | 5/1998 | Mitchell et al. ............................ 602/5 |
| 5,788,618 | 8/1998 | Joutras . |
| 5,954,621 | 9/1999 | Joutras et al. ............................ 482/114 |

*Primary Examiner*—Kim M. Lee
*Attorney, Agent, or Firm*—Alan Kamrath; Oppenheimer Wolff & Donnelly LLP

[57] ABSTRACT

The upper and lower sections (12, 14) of a splint (10) are pivotable about a pivot axis (17) by a pair of pivot assemblies (16). Each pivot assembly (16) includes a housing (18) having a cylindrical side wall (20) and a spacer (30) having a cam track (34). The housing (18) is closed by a closure plate (36) which pivotably mounts an arcuate brake shoe (46) and which mounts a cam (60). Relative rotation of the housing (18) and closure plate (36) causes the cam (60) to follow on the cam track (34) for pivoting the brake shoe (46) to engage the side wall (20) with variable braking force. In preferred forms, a compression block (80) having an aperture (82) formed therein is positioned between the brake shoe axis and the end of the brake shoe (46) to provide a visual indication of the resistance force. In preferred forms, a V-shaped projection (90) is formed on the brake shoe (46) for slideable receipt in a V-shaped groove (84) formed in the side wall (20).

26 Claims, 2 Drawing Sheets

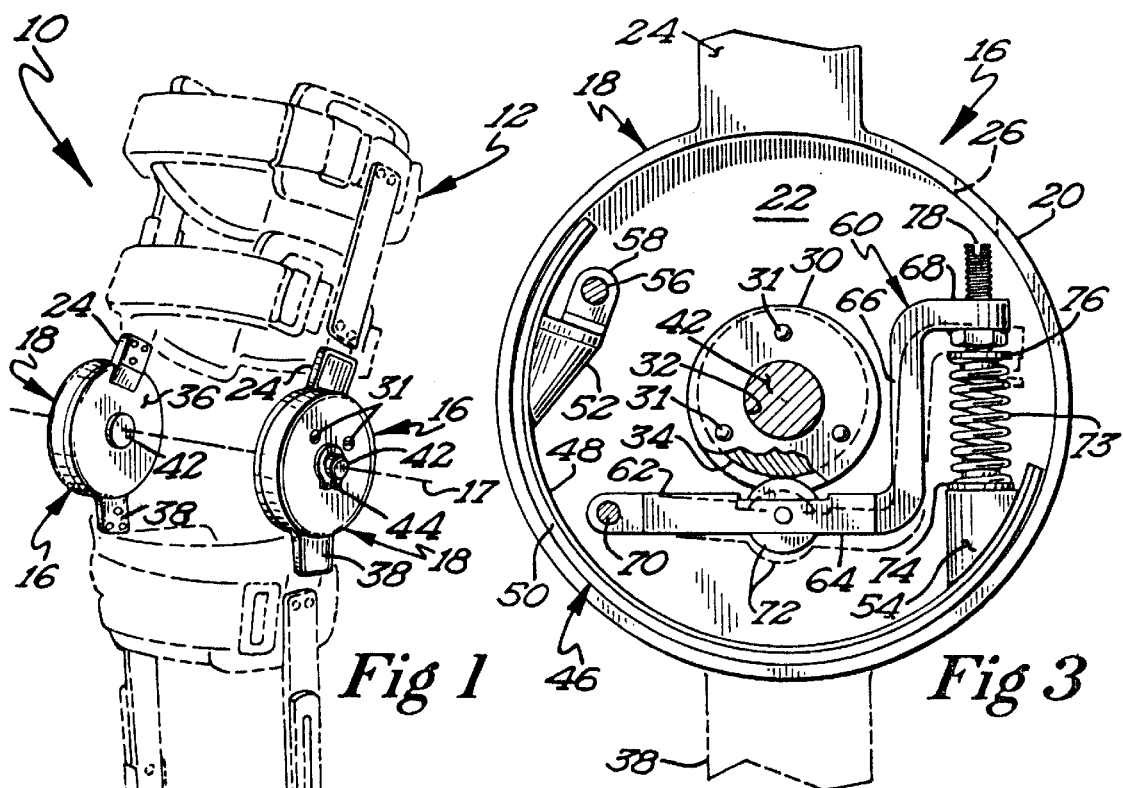
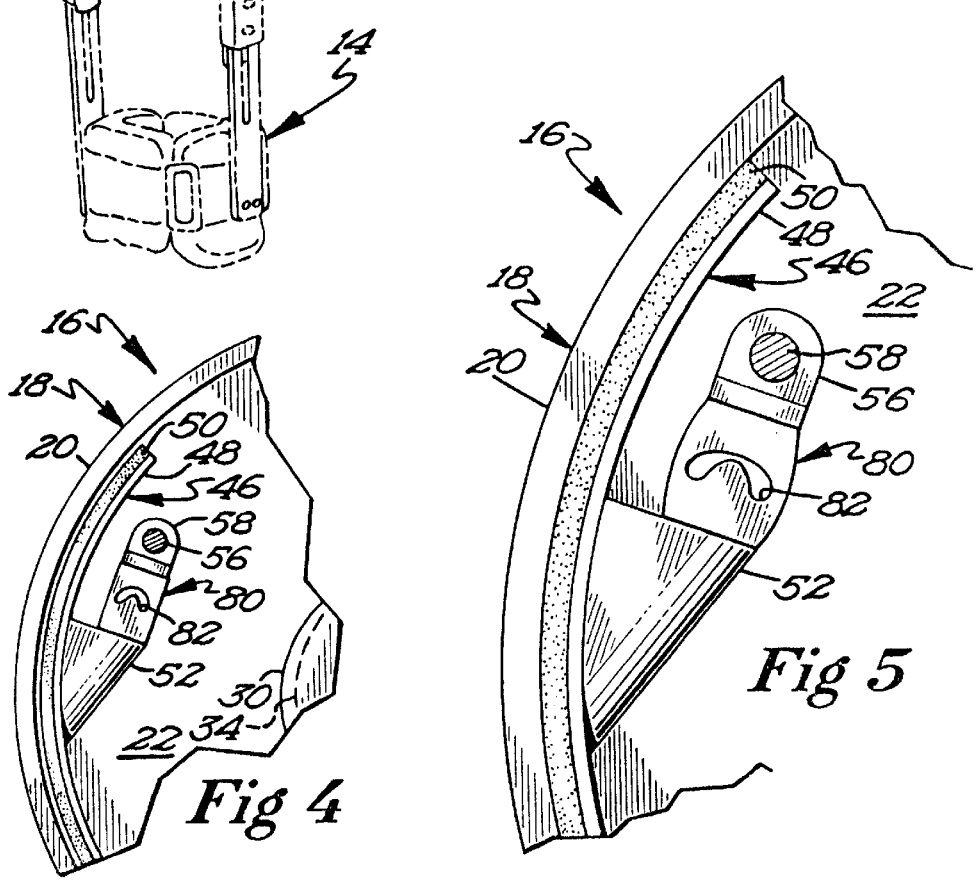

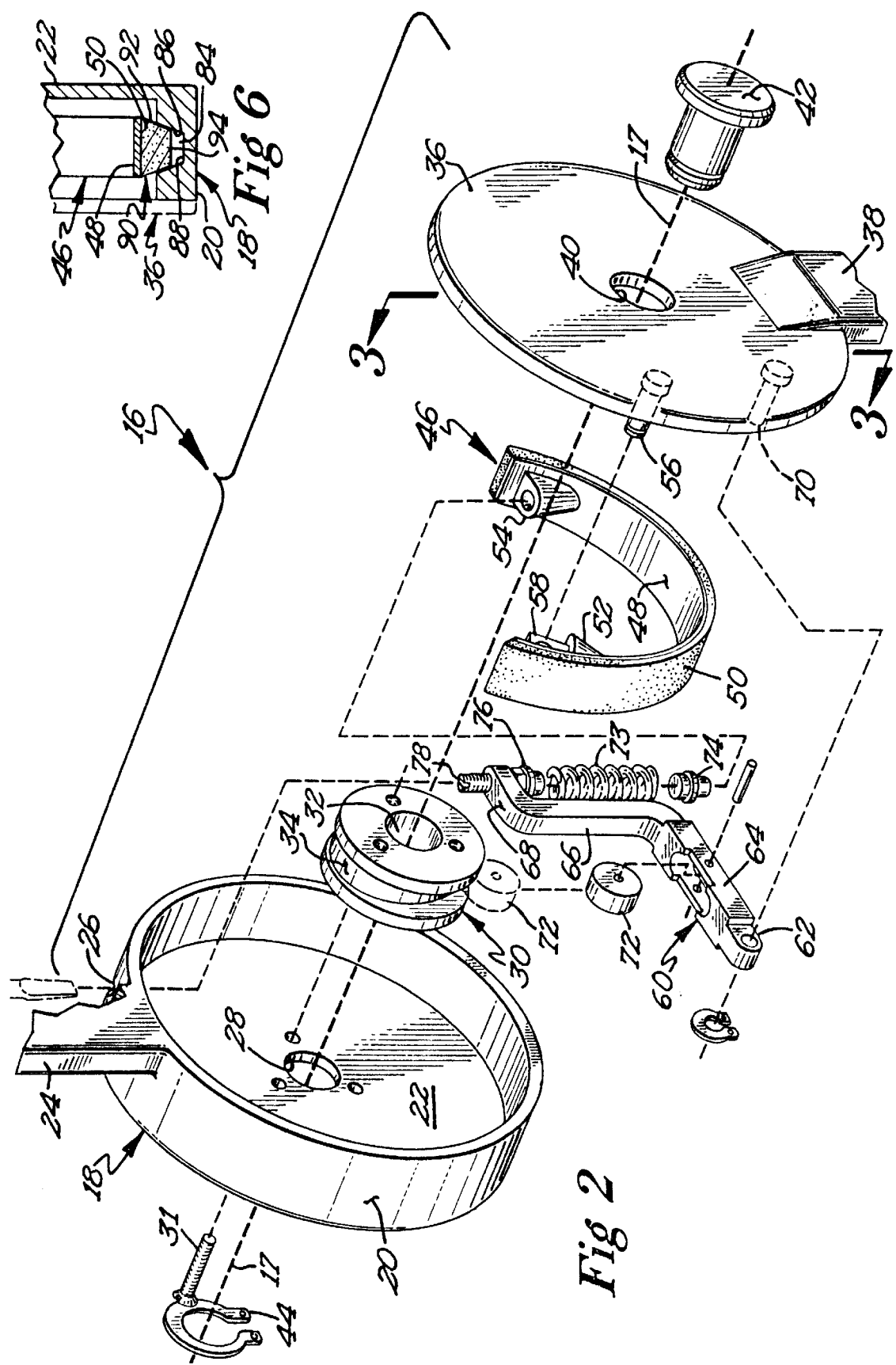

UNIDIRECTIONAL RESISTANCE PIVOT ASSEMBLY FOR A SPLINT

BACKGROUND

The present invention generally relates to an orthopedic resistance device, and specifically to a device which applies resistance to the knee in one direction and allows relatively free movement of the knee in the opposite direction.

Dysfunction of the knee joint is often a result of abnormalities caused by disease, trauma, or mechanical degradation of the anatomic structures of the knee. The abnormalities cause the knee to mechanically malfunction requiring corrective surgery or therapy. A common result of intraoperative trauma is the introduction of soft tissue constrained joint contractures of varying severity. Various dynamic knee braces are available to provide support and rehabilitation to a damaged knee. Dynamic braces are designed to improve the range of motion over which a knee can flex or extend by applying a constant torque to the knee. However, knee abnormalities can also cause muscular imbalance (poorly coordinated muscular activity) which is not corrected by a dynamic brace.

The anatomic structures of the knee may be altered sufficiently that changes in neuromuscular "motor pathways" may be needed to regain normal, pain free function. Without proper rehabilitation, the neuromuscular motor-pathways adapt very slowly to the altered structures thus creating muscular imbalance. While the flexibility of the knee can be rehabilitated using dynamic knee braces, the muscular imbalance may not be corrected and the knee is left with good flexibility but poorly coordinated muscular activity. The result is a knee with full movement yet pain and instability when moved in certain directions.

Neuromuscular re-education is a rehabilitation technique which accelerates motor pathway development by temporarily altering the amplitude and timing of forces upon the musculoskeletal structures thus altering the amplitude and timing of muscle use in performing physical motion. It is evident that there is a need for applying neuromuscular re-education of the knee via a device which imposes the appropriate musculoskeletal stimuli to the structures of the knee, specifically throughout flexion. In addition, a device which induces properly imposed forces resisting motion of the knee joint in flexion will help to properly realign the musculoskeletal structures of the knee thus providing support and alleviating pain which further accelerates the rehabilitation process. Unlike existing dynamic braces, the device would apply substantial resistance to the knee only through flexion and not through extension.

SUMMARY

The present invention solves this need and other problems in the field of rehabilitation of joint traumas by providing, in the preferred form, a pivot assembly where a force resisting pivotal movement between first and second members is provided as a result of pivotal movement of the first and second members and which is substantially larger when pivotal movement is in one direction than when pivotal movement is in the other direction. In the most preferred form, the resistance force is provided as the result of sliding frictional forces between a cylindrical sidewall of the housing of the pivot assembly and an arcuate brake shoe which is pivoted by a cam mounted on a plate pivotal relative to the housing, with the cam following a cam track which pivots relate to the cam as the result of pivotal movement of the housing relative to the plate.

It is thus an object of the present invention to provide a novel unidirectional resistance pivot assembly for a splint.

It is further an object of the present invention to provide such a novel unidirectional resistance pivot assembly which relies upon sliding friction as a result of pivotal movement to produce the resistance force.

It is further an object of the present invention to provide such a novel unidirectional resistance pivot assembly utilizing a pivotable, arcuate brake shoe located in a cylindrical housing.

It is further an object of the present invention to provide such a novel unidirectional resistance pivot assembly wherein the resistance force can be varied.

It is further an object of the present invention to provide such a novel unidirectional resistance pivot assembly providing a visual indication of the resistance force being applied.

It is further an object of the present invention to provide such a novel unidirectional resistance pivot assembly which applies a resistance force which is predictable, controllable, and reproduceable.

It is further an object of the present invention to provide such a novel unidirectional resistance pivot assembly having a brake shoe providing a multiplier effect on friction.

It is further an object of the present invention to provide such a novel unidirectional resistance pivot assembly having a brake shoe with prolonged wear capabilities.

It is further an object of the present invention to provide such a novel unidirectional resistance pivot assembly providing alignment assurance between the sliding friction engagement surfaces.

It is further an object of the present invention to provide such a novel unidirectional resistance pivot assembly which can be easily and quickly adjusted to change the degree and manner that resistance force is provided.

It is further an object of the present invention to provide such a novel unidirectional resistance pivot assembly of a simplified construction which is easy to manufacture and assemble.

These and further objects and advantages of the present invention will become clearer in light of the following detailed description of illustrative embodiments of this invention described in connection with the drawings.

DESCRIPTION OF THE DRAWINGS

The illustrative embodiments may best be described by reference to the accompanying drawings where:

FIG. 1 shows a perspective view of an orthopedic unidirectional resistance device including first and second pivot assemblies according to the preferred teachings of the present invention.

FIG. 2 shows an exploded perspective view of a pivot assembly of FIG. 1.

FIG. 3 shows a cross sectional view of a pivot assembly of FIG. 1 according to section line 3—3 of FIG. 2.

FIGS. 4 and 5 show partial, cross sectional views of an alternate form of a pivot assembly according to the preferred teachings of the present invention.

FIG. 6 shows a partial, cross sectional view of an alternate form of friction engagement surfaces for a pivot assembly according to the preferred teachings of the present invention.

All figures are drawn for ease of explanation of the basic teachings of the present invention only; the extensions of the figures with respect to number, position, relationship, and dimensions of the parts to form the preferred embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "top", "bottom", "first", "second", "inside", "outer", "upper", "lower", "height", "width", "length", "thickness", "end", "side", "inner", "horizontal", "vertical", "axial", "radial", and similar terms are used herein, it should be understood that these terms have reference only to the structure shown in the drawings as it would appear to a person viewing the drawings and are utilized only to facilitate describing the illustrative embodiments.

DESCRIPTION

An orthopedic resistance device or splint according to the preferred teachings of the present invention is shown in the drawings and generally designated 10. In the most preferred form, device 10 is illustrated and described for use in connection with a knee joint. However, it is to be understood that device 10 may be adapted according to the teachings of the present invention for use in conjunction with other body joints between limbs, such as the ankle, elbow, or wrist. Generally, device 10 includes an upper section 12 defined by a pair of upper cuff assemblies adapted to encircle the wearer's thigh and a lower section 14 defined by a pair of lower cuff assemblies adapted to encircle the lower leg of the wearer. Upper and lower sections 12 and 14 are connected together by a pair of pivot assemblies 16 to enable upper and lower sections 12 and 14 to pivot or articulate about a transverse pivot axis 17 in approximate alignment with the anatomical axis of rotation of the knee or similar joint.

Generally, each pivot assembly 16 includes a first member in the preferred form of a housing 18 having a cylindrical side wall 20 and a closed outer end 22, with the inner end being open. An arm 24 extends radially from side wall 20 adjacent to the inner end and is suitably secured to upper section 12 in any desired manner. A tool access opening 26 is formed in side wall 20. A circular pivot opening 28 is formed in closed end 22 at axis 17 of cylindrical side wall 20.

A spacer 30 is suitably removably secured to closed end 22 such as by screws 31 extending through closed end 22 and threaded into spacer 30 as shown. Spacer 30 has an axial length generally corresponding to the axial length of side wall 20. Spacer 30 also includes a cylindrical pivot opening 32 of a diameter and location corresponding to pivot opening 28 of end 22. Spacer 30 further includes a cam track 34 formed on its outer perimeter, with the cam track 34 being nonconcentric to axis 17 of openings 28 and 32 and of side wall 20.

Generally, each pivot assembly 16 further includes a second member in the preferred form of a housing closure plate 36 for closing the open end of housing 18. In the most preferred form, plate 36 is circular of a size generally corresponding to and for abutment with the open end of side wall 20. An arm 38 extends radially from plate 36 and is suitably secured to lower section 14 in any desired manner. In the preferred form, plate 36 includes a circular pivot opening 40 of a diameter corresponding to openings 28 and 32. Plate 36 is rotatably mounted to and for pivotal movement relative to housing 18 such as by a pivot pin 42 extending through openings 40, 32, and 28 and retained therein such as by a snap clip 44. Pivot pin 42 defines pivot axis 17 of pivot assembly 16.

Generally, each pivot assembly 16 further includes a brake shoe 46 of an arcuate, generally semicylindrical shape of a diameter generally corresponding to that of side wall 20. In the preferred form, brake shoe 46 includes a carrier 48 for a friction lining 50 adapted to abut and slide relative to the inside surface of side wall 20. It should be appreciated that brake shoe 46 can have other constructions according to the teachings of the present invention including but not limited to a single, integrally formed component. Carrier 48 further includes first and second mounts 52 and 54 adjacent the opposite first and second ends of brake shoe 46. The first end of brake shoe 46 is suitably pivotably mounted to closure plate 36 such as by a pivot pin 56 extending through an aperture formed in a pivot bracket 58 secured to mount 52. In the most preferred form, the brake shoe axis defined by pivot pin 56 is spaced from and parallel to pivot axis 17 and is located at generally a 10 o'clock position when arm 38 extends radially outward from a 6 o'clock position.

Generally, each pivot assembly 16 further includes suitable provisions for pivoting brake shoe 46 relative to closure plate 36 as the result of relative pivotal movement between housing 18 and closure plate 36. Particularly in the preferred form, brake shoe 46 is pivoted with pivotal movement of housing 18 and plate 36 by a cam 60 resiliently connected to brake shoe 46 and which engages cam track 34 and which is pivotably mounted to closure plate 36. In the most preferred form, cam 60 includes a cam arm 62 of a generally L-shape and specifically including a first leg 64 terminating generally perpendicularly in a second leg 66 in turn terminating generally perpendicularly in a third leg 68. Arm 62 is suitably pivotably mounted to closure plate 36 such as by a pivot pin 70 extending through an aperture formed adjacent the free end of leg 64. In the most preferred form, the cam axis defined by pivot pin 70 is spaced from and parallel to pivot axis 17 and the brake shoe axis and is located at generally a 8 o'clock position when arm 38 extends radially outward from a 6 o'clock position and thus is located on the same side of axis 17 in one direction (vertical) and is located on opposite sides of axis 17 in the other direction (horizontal) than pivot pin 56 as best seen in FIG. 3. Leg 64 extends along a chord which is parallel to a tangent of the circular perimeter of closure plate 36 at the 6 o'clock position, with leg 66 located on the opposite side of axis 17 than pivot pin 70.

Cam 60 further includes a suitable follower 72 for engaging and following cam track 34 of spacer 30. In the most preferred form, follower 72 is in the form of a roller which is rotatably mounted to leg 64 generally intermediate leg 66 and pivot pin 70 about an axis which is parallel to the axes defined by pivot pins 56 and 70 and axis 17.

Suitable provisions are provided to resiliently connect cam 60 to the second end of brake shoe 46. In the preferred form, a compression spring 73 is sandwiched between a spring retainer 74 suitably received in mount 54 of brake shoe 46 and a spring retainer 76 suitably received in leg 68 of cam 60. In the most preferred form, spring retainer 76 is threadably received in leg 68 and includes suitable provisions such as a slot 78 for receipt of a tool such as a screwdriver as partially shown in FIG. 2 for extending through opening 26 to allow threading of spring retainer 76 into or out of leg 68. According to the preferred teachings of the present invention, spring 73 is retained between retainers 74 and 76 in an easily removable manner to allow springs 73 of different compression strengths to be utilized in pivot assemblies 16 according to the teachings of the present invention. In this regard, springs 73 could be color coded or otherwise identified according to their compression strength. Although spring 73 is shown in the preferred form, other manners of resiliently connecting cam 60 to brake shoe 46 can be utilized including but not limited to a resilient block formed of rubber, urethane, or like material.

In alternate forms of the present invention, a block 80 formed of soft, elastic, or compliant material is located intermediate mount 52 at the second end of brake shoe 46 and bracket 58. One or more apertures 82 are formed through block 80. In particular, apertures 82 are designed to collapse as compression forces are placed on block 80 between mount 52 and bracket 58. Aperture 82 can be shaped to create geometries that visually indicate the amount of compression forces being applied to block 80. In the most preferred form shown, aperture 82 has a cylindrical shape but with one side including a parabolic arc having a considerably smaller diameter than aperture 82 and extending diametrically beyond the center of the cylindrical shape but without engaging the opposite side of the cylindrical shape when block 80 is not compressed as shown in FIG. 4. Compression of block 80 will result in the parabolic arc side of the shape of aperture 82 moving as shown in FIG. 5 towards and then engaging the opposite side of the cylindrical shape to define two openings which then collapse under additional compression forces.

It should be appreciated that blocks 80 having different compression strengths can be inserted intermediate mounts 52 and bracket 58 according to the level of resistance forces being applied by device 10. As an example, blocks 80 could be color coded or otherwise identified in the same manner as and for use with corresponding springs 73. Likewise, although a single aperture 82 is provided in block 80 in the form shown, more than one aperture 82 of different and differing shapes can be provided such as to allow the apertures to collapse serially with increasing compression forces. Additionally, although blocks 80 are shown in the preferred form, other structures which collapse under compression forces such as but not limited to springs as well as other provisions can be utilized to provide indication, whether visual and/or otherwise, of the resistance force being applied by device 10 according to the teachings of the present invention. It should be appreciated that the presence of such collapsing structures and the particular size and construction of such collapsing structures may also preload brake shoe 46 in combination with spring 73 of the preferred form in obtaining the desired resistance force to pivotal movement of housing 18 relative to plate 36.

Now that the basic construction of pivot assembly 16 according to the preferred teachings of the present invention has been explained, exemplary modes of operation of pivot assemblies 16 and device 10 can be set forth. In particular, upper and lower section 12 and 14 are attached to the wearer's leg in a manner that axis 17 is aligned with the anatomical axis of rotation of the knee for which rehabilitation is desired. For purposes of explanation, it will be assumed that the first position of device 10 and of the wearer's leg is initially the extension position, ie the wearer's leg is straight.

With movement of the wearer's leg from the extension position to the second or flexion position, housing 18 and plate 36 of each pivot assembly 16 in device 10 rotate relative to each other about axis 17 due to their securement to upper and lower sections 12 and 14 attached on opposite sides of the wearer's knee. With reference to FIG. 3, housing 18 will move in a clockwise direction and/or brake shoe 46 will move in a counterclockwise direction. Due to the attachment of spacer 30 to housing 18 and the attachment of cam 60 to plate 36, relative movement of housing 18 and plate 36 causes pivotal movement of cam 60 about pivot pin 70. In particular, as spacer 30 rotates relative to cam 60, follower 72 rolls upon cam track 34 to cause cam arm 62 to pivot about pivot pin 70 so that leg 68 moves in a direction toward mount 54 and brake shoe 46. Due to the movement of cam arm 62, further, compression forces are placed upon spring 73 which in turn biases brake shoe 46 to pivot about pivot pin 56 so that friction lining 50 is biased to engage with the inside surface of side wall 20 with increased force. The force at which friction lining 50 engages with side wall 20 is dependent on several factors including but not limited to the shape of cam track 34 and thus the amount of movement of leg 68 and the compression strength of spring 73. The amount of sliding frictional or braking force between brake shoe 46 and side wall 20 and thus the resistance force to pivotal movement of arms 24 and 38 and of upper and lower sections 12 and 14 about axis 17 is dependent on several factors including but not limited to the coefficient of friction between friction lining 50 and the inside surface of side wall 20 as well as the force at which friction lining 50 engages with side wall 20. In this regard, the force at which friction lining 50 engages with side wall 20 and thus the pivotal resistance force between upper and lower sections 12 and 14 can be adjustably varied by rotating spring retainer 76 in leg 68. In particular, rotating spring retainer 76 in leg 68 causing movement towards mount 54 will result in greater pivotal resistance force whereas rotating spring retainer 76 in leg 68 causing movement away from mount 54 will result in lesser pivotal resistance force between upper and lower sections 12 and 14.

In one preferred form according to the teachings of the present invention, cam track 34 is profiled so that the resistance force ramps up very quickly when device 10 moves from the extension position and then applies a relatively constant resistance force thereafter and with continued pivotal movement of device 10. However, it can be appreciated that the resistance force can be applied in any desired manner by changing the design of the profile of cam track 34 including but not limited to of increasing resistance force as device 10 moves farther from the extension position. In the most preferred form, spacer 30 is removable from housing 18 so that spacers 30 having cam tracks 34 of different profiles can be substituted according to the manner and degree that the resistance force is desired to be applied.

In a preferred form of the present invention, the therapist supervising the rehabilitation utilizing device 10 can look at apertures 82 in block 80, such as through a window, not shown, provided in housing 18, for a visual indication of the resistance force being applied by pivot assemblies 16. It can be appreciated that the resistance force desired will vary according to the particular wearer, the extent of the knee trauma, and the extent of the rehabilitation that has already occurred. In this regard, if the resistance force is not as desired, the sliding frictional force and thus the resistance force can be adjusted in the preferred form such as by extending a screw driver through opening 26 to engage slot 78 and thread spring retainer 76 into or out of leg 68. Likewise, spacers 30, springs 73, and/or blocks 80 can be interchanged to apply the desired resistance force. After adjustment, it can be confirmed that the desired resistance force is being applied by device 10 by observing the compression of apertures 82 of blocks 80 of pivot assemblies 16.

After the knee has been flexed to the flexion position of the desired angle and it is desired to return the knee to the extension position, housing 18 and plate 36 of each pivot assembly 16 in device 10 rotate relative to each other about axis 17 in the opposite direction ie with side wall 20 moving counterclockwise in direction and/or brake shoe 46 moving in a clockwise direction as shown in FIG. 3. It can be appreciated that relative rotation of side wall 20 and brake shoe 46 in that direction causes spring 73 to be compressed so that the amount of braking force between brake shoe 46 and side wall 20 and thus the resistance force to pivotal movement of arms 24 and 38 and of upper and lower sections 12 and 14 about axis 17 is reduced. Additionally, friction lining 50 can be formed of soft material and designed to have a reduced coefficient of friction with side wall 20 when side wall 20 is moved counterclockwise relative to brake shoe 46 than when side wall 20 is moved clockwise relative to brake shoe 46.

Additionally, relative rotation of housing 18 and plate 36 results in rotation of spacer 30 relative to cam 60. In particular, follower 72 rolls upon cam track 34 to cause cam arm 62 to pivot about pivot pin 70 so that leg 68 moves in a direction away from mount 54 and brake shoe 46. Due to the movement of cam arm 62, decreased compression forces are placed upon spring 73 in the preferred form so that brake shoe 46 is biased with a lesser force towards side wall 20.

Thus, according to the preferred teachings of the present invention, device 10 applies a predictable, controllable, and reproduceable resistance force as the knee is bent from the extension position and which is substantially larger than the very low, predictable, controllable, and reproduceable resistance force as the knee is moved towards the extension position. In the preferred form and due to the arcuate shape of the friction engagement surfaces provided by brake shoe 46 and side wall 22, a force couple is added to the applied braking force by cam 60 through spring 73 as a result of the direction of rotation of side wall 20 relative to brake shoe 46 while the force couple is subtracted from the applied braking force when the direction of relative rotation is reversed. This concept is further enhanced due to the maximization of the forward to back friction ratio of friction lining 50. Thus, although a zero return resistance force is not obtained in the preferred form, pivot assemblies 16 significantly reduce resistance force to come closer to a one way drive. Additionally, such resistance force is a result of pivotal movement of housing 18 relative to plate 36 and in particular as a result of sliding frictional forces between brake shoe 46 and side wall 20. It can then be appreciated that the resistance force is not created as the result of energy storage devices such as but not limited to springs, rachets, or the like. Thus, pivot assemblies 16 are of a simplified construction which are easy to manufacture and assemble as well as having the ability to quickly interchange components to change the degree as well as manner that the resistance force is provided.

Now that the basic teachings of the present invention have been explained, many extensions and variations will be obvious to one having ordinary skill in the art. For example, although shown as being generally planar at least in FIG. 2, the inside surface of side wall 20 and the engagement surface of friction lining 50 can be shaped to achieve desired results. As an example, FIG. 6 shows an alternate embodiment where the inside surface of side wall 20 includes a V-shaped groove 84 having side surfaces 86 terminating in a relatively flat bottom surface 88. Similarly, friction lining 50 includes a V-shaped projection 90 having side surfaces 92 terminating in a relative flat outer surface 94. The angle between side surfaces 86 of groove 84 is generally equal to the angle between side surfaces 92 of projection 90. It should be appreciated that projection 90 of brake shoe 46 is received and slideable in groove 84 of side wall 20 in a manner that surfaces 92 engage with surfaces 86 while surface 94 is spaced from surface 88.

Shaping side wall 20 and friction lining 50 to include groove 84 and projection 90 achieves many advantages. In particular, alignment assurance is provided by the friction interfacing surfaces of side wall 20 and friction lining 50 by the receipt of projection 90 in groove 84. Also, as friction lining 50 wears from side surfaces 92, projection 90 will extend farther into groove 84 so that surfaces 88 and 94 move together with increasing wear. Thus, prolonged wear capabilities are achieved. Additionally, the engagement area between side surfaces 86 and 92 can be relatively larger than with planar engagement surfaces. Thus, a multiplier effect is achieved on the frictional force between brake shoe 46 and side wall 20 and thus also on the resistance force applied by device 10 according to the teachings of the present invention. This increased friction force can allow the axial length of side wall 20 and of brake shoe 46 to be reduced to thereby minimize the overall size of pivot assemblies 16 without reducing the desired resistance force applied by device 10.

Although only a single projection 90 and groove 84 is provided in the preferred form shown, more than one projection 90 and groove 84 can be utilized according to the teachings of the present invention such as in a W configuration. Provisions can be made to include engagement between side wall 20 and friction lining 50 axially outward of groove 84 and projection 90 and/or between multiple grooves 84 and projections 90, if desired, but with a potential loss of the multiplier effect on the frictional forces.

Additionally, although in the preferred form side surfaces 86 and 92 are shown as being linearly straight, side surfaces 86 and 92 can have other geometries for increasing the gripping power between brake shoe 46 and side wall 20 including but not limited to curved shapes. Further, the geometries of side surfaces 86 and 92 can be shaped in a manner to cooperate with the material from which friction lining 50 is formed to enhance the forward to back friction ratio to come close to a one way drive.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A pivot assembly comprising, in combination: a first member; a second member; means for mounting the first member for pivotal movement relative to the second member about a pivot axis between a first position and a second position; and means for providing a force to resist pivotal movement of the first and second members as a result of pivotal movement of the first and second members, with the resistance force being substantially larger when pivotal movement is from the first position than when pivotal movement is towards the first position; wherein the resistance force providing means comprises means for providing sliding frictional forces to resist pivotal movement of the first and second members, with the sliding frictional forces being substantially larger when pivotal movement is from the first position than when pivotal movement is towards the first position.

2. The pivot assembly of claim 1 wherein the sliding frictional forces providing means comprises, in combination: a friction engagement surface carried by the first member; and a brake shoe carried by the second member for engagement with the friction engagement surface, with the brake shoe and friction engagement surface being movable relative to each other as a result of pivotal movement of the first and second members.

3. The pivot assembly of claim 2 wherein one of the friction engagement surface and the brake shoe includes at least a first groove and the other of the friction engagement surface and the brake shoe includes a projection for slideable receipt in the groove.

4. The pivot assembly of claim 2 wherein the friction engagement surface and the brake shoe are generally arcuately shaped.

5. The pivot assembly of claim 4 wherein the friction engagement surface is cylindrical shaped and defines a housing for the pivot assembly, with the second member being in the form of a plate for closing the housing.

6. The pivot assembly of claim 4 wherein the brake shoe includes a first end and a second end, with the first end of the brake shoe being pivotably mounted to the second member about a brake shoe axis spaced from and parallel to the pivot axis; and wherein the sliding frictional forces providing means further comprises, in combination: means for pivoting the brake shoe about the shoe axis with pivotal movement of the first and second members.

7. The pivot assembly of claim 6 wherein the pivoting means comprises, in combination: a cam track mounted to the first member; and a cam mounted to the second member for engaging the cam track, with the cam being connected to the brake shoe.

8. The pivot assembly of claim 7 wherein the cam comprises, in combination: a cam arm pivotably mounted to the second member about a cam axis spaced from and parallel to the pivot axis, with the cam arm including a follower for engaging the cam track; and means for resiliently connecting the second end of the brake shoe to the cam arm.

9. The pivot assembly of claim 8 wherein the resiliently connecting means includes means for adjusting the sliding frictional forces provided to resist pivotal movement of the first and second members.

10. The pivot assembly of claim 8 wherein the resiliently connecting means comprises a compression spring sandwiched between the cam arm and the second end of the brake shoe.

11. The pivot assembly of claim 10 wherein the cam arm includes a first leg terminating in a second leg in turn terminating in a third leg, with the first leg having a free end pivotally mounted to the second member, with the spring being sandwiched between the third leg and the second end of the brake shoe, with the cam axis located on the opposite side of the pivot axis than the third leg.

12. The pivot assembly of claim 6 further comprising, in combination: means for providing a visual indication of the force being provided to resist pivotal movement of the first and second members comprising, in combination: a compression member positioned between the brake shoe axis and the first end of the brake shoe; and means for visually indicating the compression of the compression member.

13. The pivot assembly of claim 12 wherein the compression member comprises a block formed of compliant material; and wherein the visually indicating means comprises at least one aperture formed through the block.

14. The pivot assembly of claim 13 wherein the aperture has a cylindrical shape but with one side including a parabolic arc having a considerably smaller diameter than the cylindrical shape and extending diametrically beyond the center of the cylindrical shape but without engaging the opposite side of the cylindrical shape when the block is not compressed.

15. The pivot assembly of claim 4 wherein one of the friction engagement surface and the brake shoe includes at least a first groove and the other of the friction engagement surface and the brake shoe includes a projection for slideable receipt in the groove.

16. The pivot assembly of claim 2 wherein the brake shoe includes a first end and a second end, with the first end of the brake shoe being pivotably mounted to the second member about a brake shoe axis spaced from and parallel to the pivot axis; and wherein the sliding frictional forces providing means further comprises, in combination: means for pivoting the brake shoe about the shoe axis with pivotal movement of the first and second members.

17. The pivot assembly of claim 16 wherein the pivoting means comprises, in combination: a cam track mounted to the first member; and a cam mounted to the second member for engaging the cam track, with the cam being connected to the brake shoe.

18. The pivot assembly of claim 16 further comprising, in combination: means for providing a visual indication of the force being provided to resist pivotal movement of the first and second members comprising, in combination: a compression member positioned between the brake shoe axis and the first end of the brake shoe; and means for visually indicating the compression of the compression member.

19. The pivot assembly of claim 1 further comprising, in combination: means for providing a visual indication of the force being provided to resist pivotal movement of the first and second members comprising, in combination: a compression member which compresses as a function of sliding frictional forces being provided; and means for visually indicating the compression of the compression member.

20. The pivot assembly of claim 19 wherein the compression member comprises a block formed of compliant material; and wherein the visually indicating means comprises at least one aperture formed through the block.

21. A pivot assembly for a splint across a body joint between first and second limbs comprising, in combination: a first member adapted to be attached to the first limb; a second member adapted to be attached to the second limb; means for mounting the first member for pivotal movement relative to the second member about a pivot axis between a first position and a second position; a generally arcuately shaped friction engagement surface carried by the first member; and a generally arcuately shaped brake shoe carried by the second member for sliding engagement with the generally arcuately shaped friction engagement surface, with the generally arcuately shaped brake shoe and generally arcuately shaped friction engagement surface being movable relative to each other for providing sliding frictional forces to resist pivotal movement of the first and second members.

22. The pivot assembly of claim 21 wherein the friction engagement surface is cylindrical shaped and defines a housing for the pivot assembly, with the second member being in the form of a plate for closing the housing.

23. The pivot assembly of claim 21 wherein one of the friction engagement surface and the brake shoe includes at least a first groove and the other of the friction engagement surface and the brake shoe includes a projection for slideable receipt in the groove.

24. The pivot assembly of claim 21 wherein the brake shoe includes a first end and a second end, with the first end of the brake shoe being pivotably mounted to the second member about a brake shoe axis spaced from and parallel to the pivot axis; and wherein the pivot assembly further comprises, in combination: a cam track mounted to the first member; and a cam mounted to the second member for engaging the cam track, with the cam being connected to the brake shoe.

25. The pivot assembly of claim 24 wherein the cam comprises, in combination: a cam arm pivotably mounted to the second member about a cam axis spaced from and parallel to the pivot axis, with the cam arm including a follower for engaging the cam track; and means for resiliently connecting the second end of the brake shoe to the cam arm.

26. The pivot assembly of claim 21 wherein the brake shoe includes a first end and a second end, with the first end of the brake shoe being pivotably mounted to the second member about a brake shoe axis spaced from and parallel to the pivot axis; and wherein the pivot assembly further comprises, in combination: means for providing a visual indication of the force being provided to resist pivotal movement of the first and second members comprising, in combination: a compression member positioned between the brake shoe axis and the first end of the brake shoe; and means for visually indicating the compression of the compression member.

* * * * *